(12) United States Patent
Shimizu

(10) Patent No.: US 6,678,053 B2
(45) Date of Patent: Jan. 13, 2004

(54) SENSOR UTILIZING ATTENUATED TOTAL REFLECTION

(75) Inventor: Hitoshi Shimizu, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 28 days.

(21) Appl. No.: 10/026,604

(22) Filed: Dec. 27, 2001

(65) Prior Publication Data

US 2002/0080358 A1 Jun. 27, 2002

(30) Foreign Application Priority Data

Dec. 27, 2000  (JP) ........................................ 2000-398309

(51) Int. Cl.⁷ .............................................. G01N 21/55
(52) U.S. Cl. ...................................................... 356/445
(58) Field of Search ................................. 356/445–448

(56) References Cited

U.S. PATENT DOCUMENTS

| | | | |
|---|---|---|---|
| 4,844,613 A | | 7/1989 | Batchelder et al. |
| 5,229,833 A | * | 7/1993 | Stewart ........................ 356/364 |
| 5,313,264 A | * | 5/1994 | Ivarsson et al. ............... 356/73 |
| 5,485,277 A | | 1/1996 | Foster |
| 6,268,125 B1 | * | 7/2001 | Perkins ........................... 435/5 |
| 6,417,925 B1 | * | 7/2002 | Naya ........................... 356/445 |
| 6,480,282 B1 | * | 11/2002 | Chinowsky et al. ......... 356/445 |

FOREIGN PATENT DOCUMENTS

| | | |
|---|---|---|
| JP | 6-167443 | 6/1994 |
| JP | 11-326194 | 11/1999 |

OTHER PUBLICATIONS

Abstract No. JP 11326194, Nov. 26, 1999.
Abstract No. JP 6167443, Jun. 14, 1994.
Surface Refracto–Sensor Using Evanescent Waves Principles and Instrumentations, Takayuki Okamoto, Optical Engineering Laboratory The Institute of Physical and Chemical Research (RIKEN) (Received Dec. 8, 1997), "Spectral Researches" vol. 47, No. 1, 1998.

* cited by examiner

Primary Examiner—Michael P. Stafira
(74) Attorney, Agent, or Firm—Sughrue Mion, PLLC

(57) ABSTRACT

A sensor utilizing attenuated total reflection is equipped with a dielectric block, a thin film layer formed on a surface of the dielectric block, an optical system for making a light beam enter the dielectric block at various angles of incidence so that the condition for total internal reflection is satisfied at an interface between the dielectric block and the thin film layer, a photodetector for detecting the light beam satisfying total internal reflection at the interface, and a differential amplifier array for differentiating a signal output from each of the light-receiving elements of the photodetector, in the juxtaposed direction of the light-receiving elements. Every time a measurement is made, a quantity change $\Delta I'$ in the differentiated value $I'$ is found by subtracting an initial value from the differentiated value $I'$. The quantity change $\Delta I'$ is amplified, so that measurements can be made without saturating subsequent electric circuits.

11 Claims, 13 Drawing Sheets

F I G. 3A
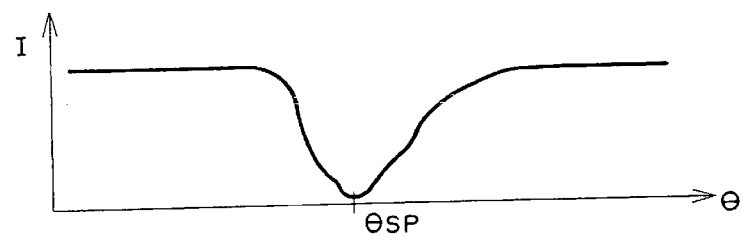
F I G. 3B
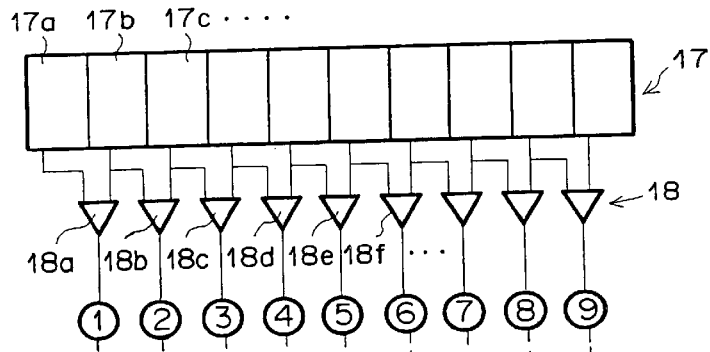
F I G. 3C
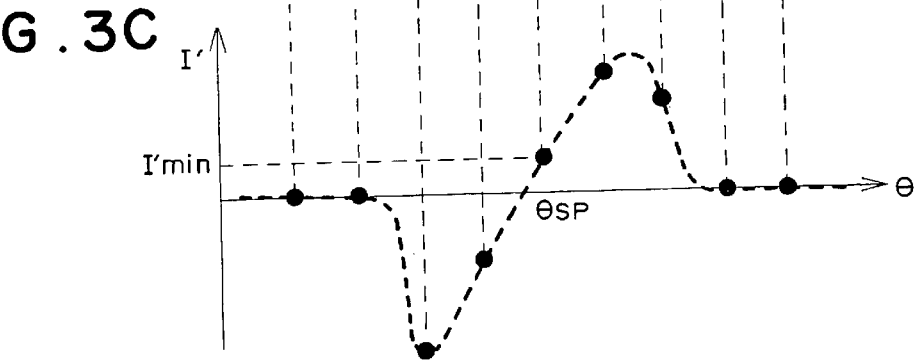

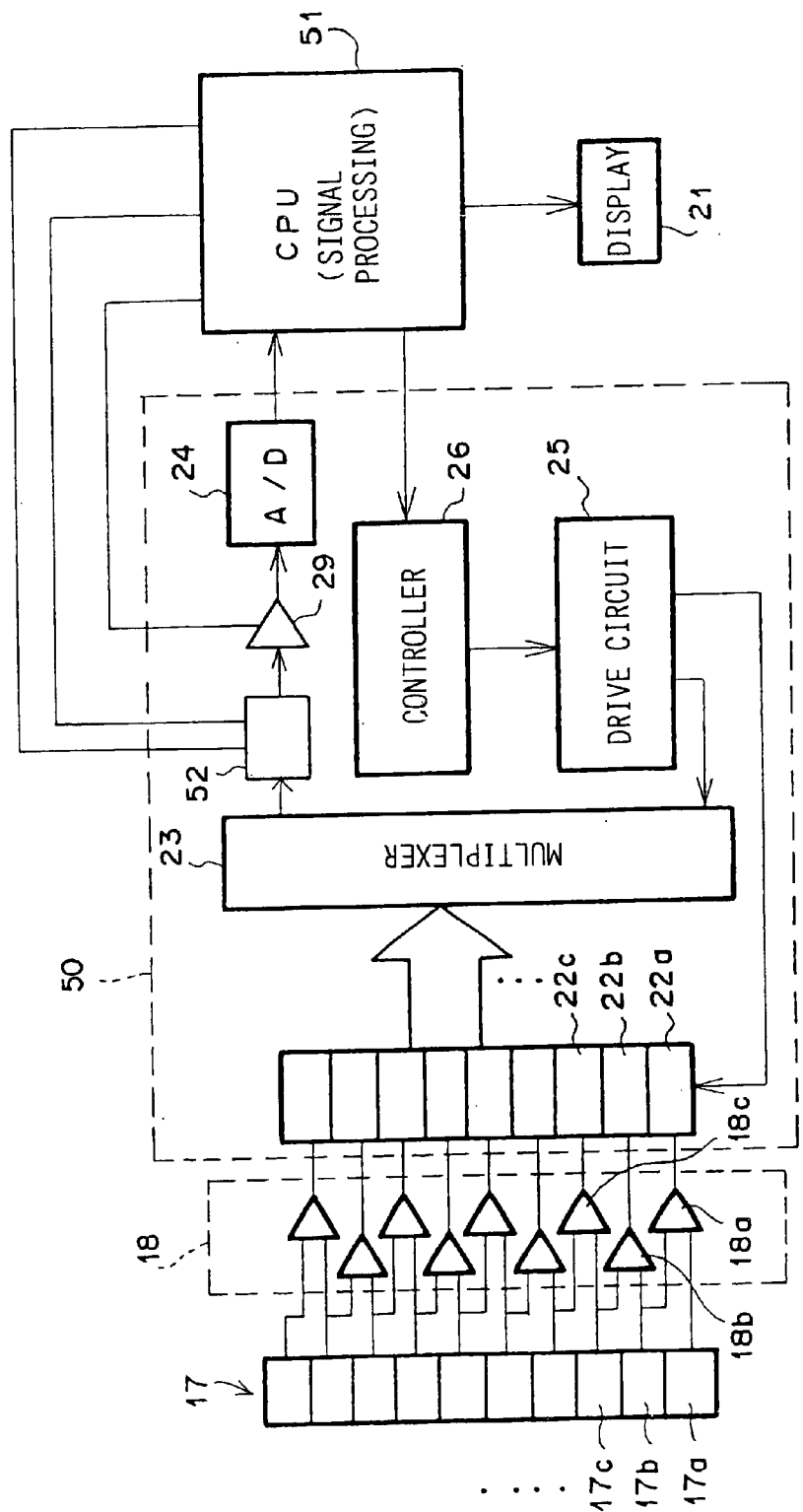
F I G. 6

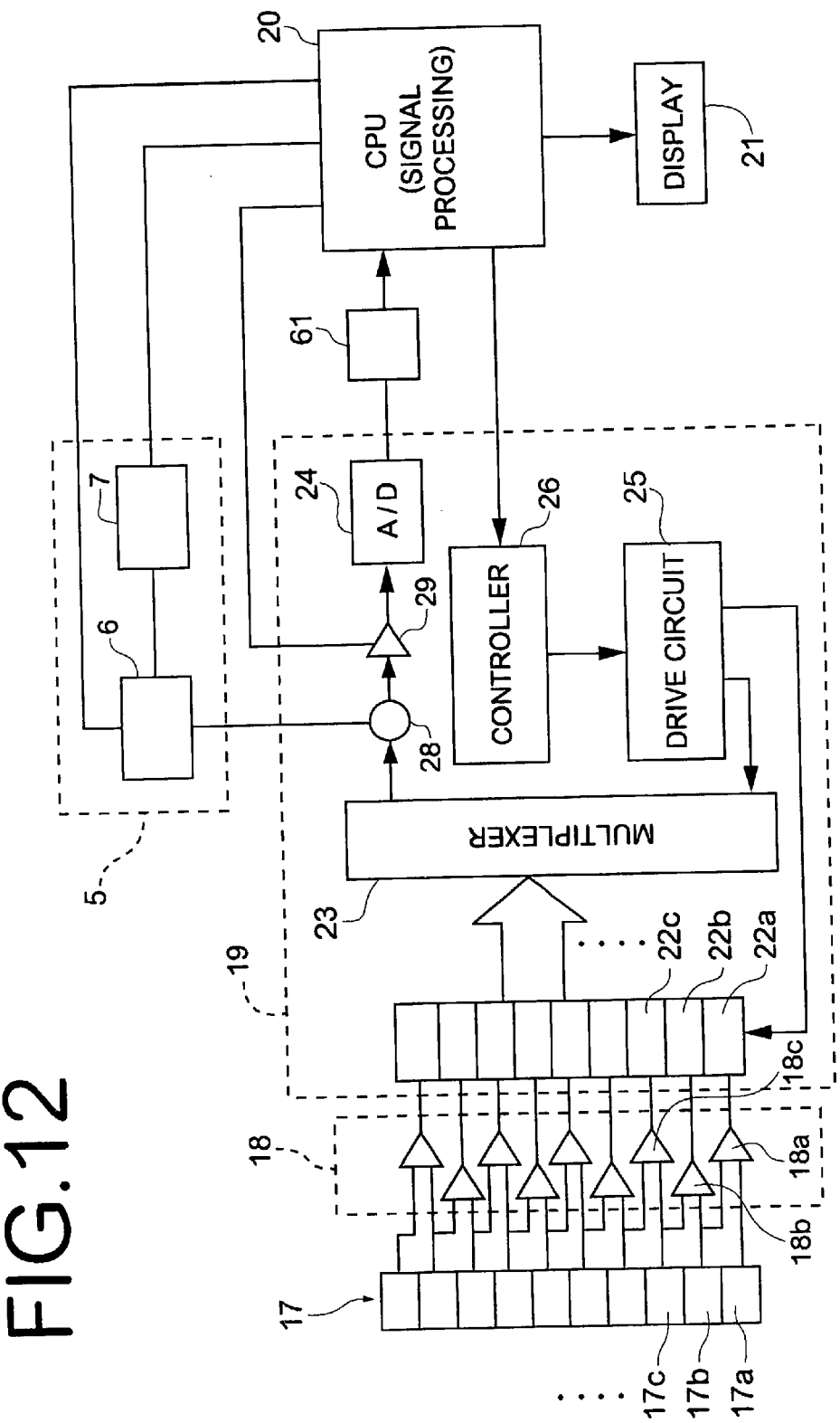

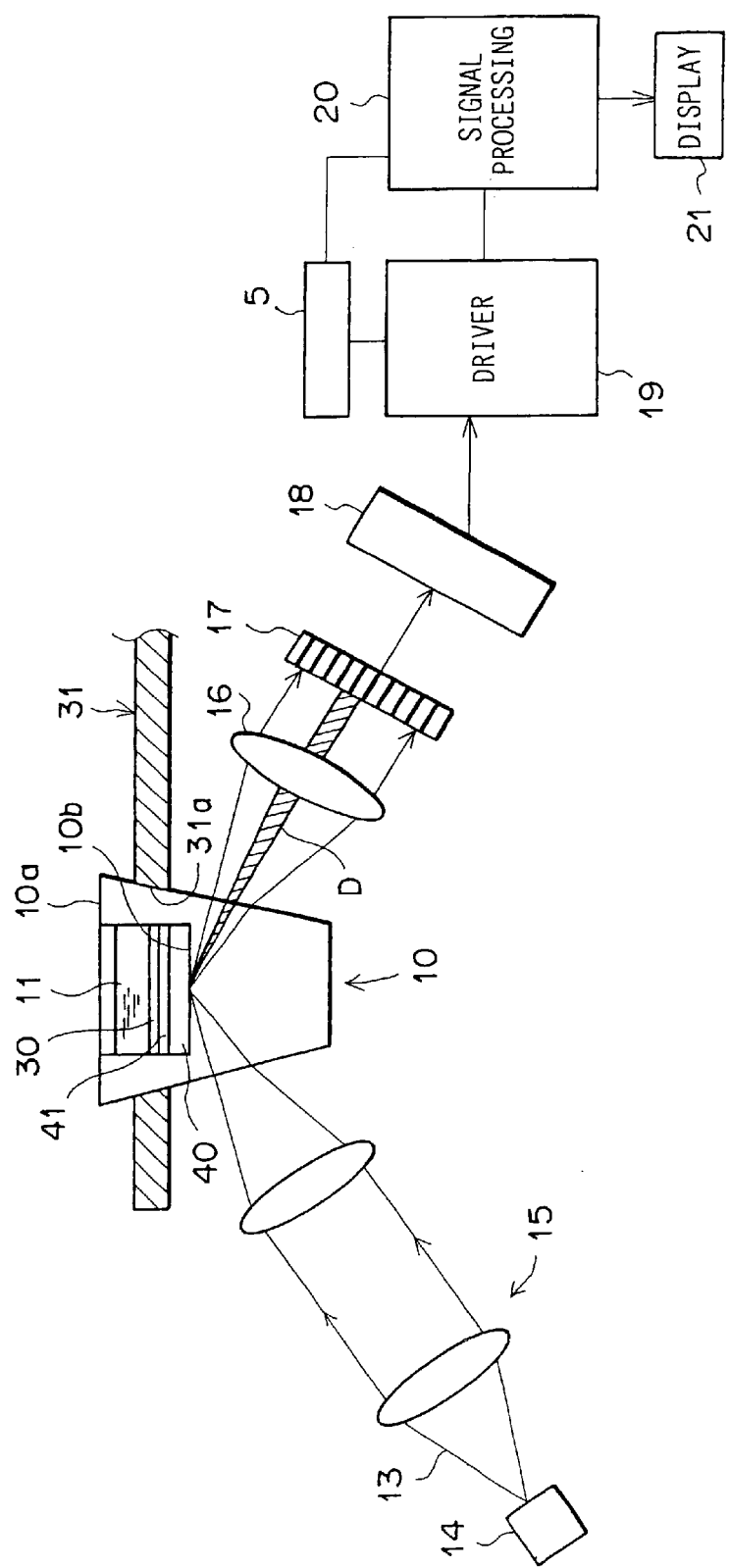

SENSOR UTILIZING ATTENUATED TOTAL REFLECTION

BACKGROUND OF THE INVENTION

1. Field of the Invention

The present invention relates to a sensor utilizing attenuated total reflection (hereinafter referred to as ATR), such as a surface plasmon resonance sensor for quantitatively analyzing a substance in a sample by utilizing excitation of a surface plasmon, and more particularly to a sensor, utilizing ATR, of a type that detects a dark line occurring in a reflected light beam due to ATR by the use of photodetection means consisting of a plurality of light-receiving elements juxtaposed in a predetermined direction.

2. Description of the Related Art

In metals, if free electrons are caused to vibrate in a group, compression waves called plasma waves will be generated. The compression waves generated in a metal surface are quantized and called a surface plasmon.

A variety of surface plasmon resonance sensors have been proposed for quantitatively analyzing a substance in a sample by taking advantage of a phenomenon that a surface plasmon is exited by light waves. Among such sensors, one employing a system called "Kretschmann configuration" is particularly well known (e.g., see Japanese Unexamined Patent Publication No. 6(1994)-167443).

The surface plasmon resonance sensor employing the "Kretschmann configuration" is equipped mainly with a dielectric block formed, for example, into the shape of a prism; a metal film, formed on a surface of the dielectric block, for placing a sample thereon; a light source for emitting a light beam; an optical system for making the light beam enter the dielectric block at various angles of incidence so that the condition for total internal reflection is satisfied at the interface between the dielectric block and the metal film; and photodetection means for detecting the state of the surface plasmon resonance, that is, the state of ATR, by measuring the intensity of the light beam satisfying total internal reflection at the interface.

In order to obtain various angles of incidence, as described above, a relatively thin light beam may be caused to strike the above-mentioned interface at different angles of incidence, or relatively thick convergent or divergent rays may be caused to strike the interface so that they contain components incident at various angles. In the former, the light beam whose reflection angle varies with a change in the incidence angle of the incident light beam can be detected by a small photodetector that is moved in synchronization with the variation in the reflection angle, or by an area sensor extending in the direction in which the angle of reflection varies. In the latter, on the other hand, rays reflected at various angles can be detected by an area sensor extending in the direction in which all the reflected rays can be received.

In the surface plasmon resonance sensor mentioned above, if a light beam strikes the metal film at a specific incidence angle $\theta_{sp}$ equal to or greater than a critical angle of incidence at which total internal reflection takes place, evanescent waves having electric field distribution are generated in the sample in contact with the metal film, whereby a surface plasmon is excited at the interface between the metal film and the sample. When the wave vector of the evanescent light is equal to the wave number of the surface plasmon and therefore the wave numbers between the two are matched, the evanescent waves and the surface plasmon resonate and light energy is transferred to the surface plasmon, whereby the intensity of light satisfying total internal reflection at the interface between the dielectric block and the metal film drops sharply. The sharp intensity drop is generally detected as a dark line by the above-mentioned photodetection means.

Note that the above-mentioned resonance occurs only when the incident light beam is a p-polarized light beam. Therefore, in order to make the resonance occur, it is necessary that a light beam be p-polarized before it strikes the interface.

If the wave number of the surface plasmon is found from an incidence angle $\theta_{sp}$ at which ATR takes place, the dielectric constant of a sample can be obtained by the following Equation:

$$K_{sp}(\omega) = (\omega/c)\{\in_m(\omega)\in_s\}^{1/2}/\{\in_m(\omega)+\in_s\}^{1/2}$$

where $K_{sp}$ represents the wave number of the surface plasmon, $\omega$ represents the angular frequency of the surface plasmon, c represents the speed of light in vacuum, and $\in_m$ and $\in_s$ represent the dielectric constants of the metal and the sample, respectively.

If the dielectric constant $\in_s$ of the sample is found, the density of a specific substance in the sample is found based on a predetermined calibration curve, etc. As a result, by finding the incidence angle $\theta_{sp}$ at which the intensity of reflected light drops, the dielectric constant of the sample, that is, the properties of the sample related to the refractive index thereof can be specified.

In this kind of surface plasmon resonance sensor, photodetection means in the form of an array can be employed with the object of measuring the aforementioned incidence angle $\theta_{sp}$ with a high degree of accuracy and in a large dynamic range, as disclosed in Japanese Unexamined Patent Publication No. 11(1999)-326194. The photodetection means is formed by a plurality of light-receiving elements juxtaposed in a predetermined direction. The light-receiving elements are disposed to respectively receive the components of a light beam satisfying total internal reflection at various angles of reflection at the aforementioned interface.

In that case, differentiation means is provided for differentiating the photodetection signals output by the light-receiving elements of the aforementioned photodetection means, in the direction where the light-receiving elements are juxtaposed. The properties of the sample related to the refractive index thereof are often analyzed based on differentiated values output by the differentiation means, particularly the differentiated value corresponding to a dark line that occurs in a reflected light beam.

In addition, a leaky mode sensor is known as a similar sensor making use of ATR, as disclosed, for instance, in "Spectral Researches," Vol. 47, No. 1 (1998), pp. 21 to 23 and pp. 26 and 27. The leaky mode sensor is constructed mainly of a dielectric block in the form of a prism, for example; a cladding layer formed on a surface of the dielectric block; an optical waveguide layer, formed on the cladding layer, for placing a sample thereon; a light source for emitting a light beam; an optical system for making the light beam enter the dielectric block at various angles of incidence so that the condition for total internal reflection is satisfied at the interface between the dielectric block and the cladding layer; and photodetection means for detecting the excited state of the waveguide mode, that is, the state of ATR by measuring the intensity of the light beam satisfying total internal reflection at the interface between the dielectric block and the cladding layer.

In the leaky mode sensor with the construction mentioned above, if a light beam falls on the cladding layer through the dielectric block at angles of incidence equal to or greater than an angle of incidence at which total internal reflection takes place, the light beam is transmitted through the cladding layer and then only light with a specific wave number, incident at a specific angle, is propagated in the optical waveguide layer in a waveguide mode. If the waveguide mode is excited in this manner, the greater part of the incident light is confined within the optical waveguide layer, and consequently, ATR occurs in which the intensity of light satisfying total internal reflection at the above-mentioned interface drops sharply. Since the wave number of light propagating in the optical waveguide layer depends on the refractive index of the sample on the optical waveguide layer, the refractive index of the sample and/or the properties of the sample related to the refractive index thereof can be analyzed by finding the above-mentioned specific angle of incidence at which ATR takes place.

The leaky mode sensor also can employ the aforementioned photodetection means in the form of an array in order to detect the position of a dark line occurring in the reflected light by ATR. In addition, the aforementioned differentiation means is often employed along with the photodetection means.

In the field of pharmaceutical research, etc., the above-mentioned surface plasmon resonance sensor and leaky mode sensor are sometimes used in a random screening method of finding a specific substance that couples with a desired sensing medium. In this case, a sensing medium is placed on the aforementioned thin film layer (i.e., the metal film in the case of the surface plasmon resonance sensor, or the cladding layer and the optical waveguide layer in the case of the leaky mode sensor), and various solutions of substances (liquid sample) are added to the sensing medium, and each time a predetermined time elapses, the aforementioned differentiated value is measured. If the added substances are coupled with the sensing medium, the refractive index of the sensing medium varies with the lapse of time by the coupling. Therefore, by detecting the above-mentioned differentiated value every time a predetermined time elapses and then judging whether or not the differentiated value has been varied, it can be judged whether or not the added substances and the sensing medium have been coupled, that is, whether or not the added substances are specific substances that couple with the sensing medium. In this case, both the sensing medium and the liquid sample are samples to be analyzed. As such a combination of specific substances and a sensing medium, there is, for example, a combination of an antigen and an antibody.

A change in the differentiated value for each predetermined time, incidentally, is slight. Therefore, to measure a slight change in the differentiated value with a high degree of accuracy, it is desirable to amplify and detect the differentiated value with amplification means. However, the differentiated value corresponding to a dark line that occurs in a reflected light beam becomes a value corresponding to the positional relationship between the photodetection element and the dark line, and even if a differentiated value whose absolute value is smallest is selected, there is a fluctuation in the value. Because of this, in the case where the degree of amplification is great and the absolute value of the differentiated value is also great, there is a fear that subsequent electric circuits will be saturated. For this reason, sufficient amplification had not been able to be performed and measurements had not been able to be made with high sensitivity.

SUMMARY OF THE INVENTION

The present invention has been made in view of the circumstances mentioned above. Accordingly, it is the primary object of the present invention to provide a sensor, utilizing ATR, which is capable of accurately analyzing a sample by measuring a change with the lapse of time in a differentiated value with high sensitivity.

To achieve this end and in accordance with an important aspect of the present invention, there is provided a sensor utilizing attenuated total reflection, comprising:

a dielectric block;

a thin film layer, formed on a surface of the dielectric block, for placing a sample thereon;

a light source for emitting a light beam;

an optical system for making the light beam enter the dielectric block at various angles of incidence so that a condition for total internal reflection is satisfied at an interface between the dielectric block and the thin film layer;

photodetection means, comprising a plurality of light-receiving elements juxtaposed in a predetermined direction and disposed to respectively receive components of the light satisfying the total internal reflection condition at the interface, for detecting the attenuated total reflection;

differentiation means for differentiating a photodetection signal output from each of the light-receiving elements of the photodetection means, in the juxtaposed direction of the light-receiving elements, and then outputting a differentiated value; and measurement means for subtracting an initial value from the differentiated value near a point where a change in the photodetection signal in the juxtaposed direction of the light-receiving elements makes a transition from decrease to increase, and then measuring a change with the lapse of time in the differentiated value from which the initial value has been subtracted.

In accordance with another important aspect of the present invention, there is provided a sensor utilizing attenuated total reflection, comprising:

a dielectric block;

a thin film layer, formed on a surface of the dielectric block, for placing a sample thereon;

a light source for emitting a light beam;

an optical system for making the light beam enter the dielectric block at various angles of incidence so that a condition for total internal reflection is satisfied at an interface between the dielectric block and the thin film layer;

photodetection means, comprising a plurality of light-receiving elements juxtaposed in a predetermined direction and disposed to respectively receive components of the light satisfying the total internal reflection condition at the interface, for detecting the attenuated total reflection caused by surface plasmon resonance;

differentiation means for differentiating a photodetection signal output from each of the light-receiving elements of the photodetection means, in the juxtaposed direction of the light-receiving elements, and then outputting a differentiated value; and measurement means for subtracting an initial value from the differentiated value near a point where a change in the photodetection signal in the juxtaposed direction of the light-receiving elements makes a transition from decrease to increase, and then measuring a change with the lapse of time in the differentiated value from which the initial value has been subtracted.

In accordance with still another important aspect of the present invention, there is provided a sensor utilizing attenuated total reflection, comprising:

a dielectric block;

a cladding layer formed on a surface of the dielectric block;

an optical waveguide layer, formed on a surface of the cladding layer, for placing a sample thereon;

a light source for emitting a light beam;

an optical system for making the light beam enter the dielectric block at various angles of incidence so that a condition for total internal reflection is satisfied at an interface between the dielectric block and the thin film layer;

photodetection means, comprising a plurality of light-receiving elements juxtaposed in a predetermined direction and disposed to respectively receive components of the light satisfying the total internal reflection condition at the interface, for detecting the attenuated total reflection caused by excitation of a waveguide mode in the optical waveguide layer;

differentiation means for differentiating a photodetection signal output from each of the light-receiving elements of the photodetection means, in the juxtaposed direction of the light-receiving elements, and then outputting a differentiated value; and measurement means for subtracting an initial value from the differentiated value near a point where a change in the photodetection signal in the juxtaposed direction of the light-receiving elements makes a transition from decrease to increase, and then measuring a change with the lapse of time in the differentiated value from which the initial value has been subtracted.

In the aforementioned sensors utilizing attenuated total reflection (ATR), it is preferable that the "differentiated value near a point where a change in the photodetection signal makes a transition from decrease to increase" be a differentiated value closest to a point where a change in the photodetection signal makes a transition from decrease to increase. However, the present invention is not limited to the differentiated value closest to the point. The differentiated value may be a differentiated value near a point where a change in the photodetection signal makes a transition from decrease to increase. The aforementioned "initial value" may employ the value of a differentiated value near a point where a change in the photodetection signal makes a transition from decrease to increase. Alternatively, by performing an arithmetic process such as feedback at the time of the start of measurements and then finding a value which shifts a measured value at the time of the start of measurements to the vicinity of 0, it may be set as an initial value. In doing subtraction, an initial value is subtracted from the differentiated value near a point where a change in the photodetection signal makes a transition from decrease to increase, by the use of a subtracter, etc. Furthermore, subtraction may be done by finding a difference between the two with a differential circuit, etc.

In the sensor of the present invention, it is preferable that the differentiation means output a difference between the optical signals output from two adjacent light-receiving elements of the photodetection means. It is also preferable that the photodetection means be a photodiode array.

In the sensor of the present invention, the aforementioned differentiation means can employ an analog circuit. In addition, the aforementioned measurement means may perform the subtraction by an analog circuit, and after A/D conversion is performed on the differentiated value from which the initial value has been subtracted, the measurement is made by a digital circuit. The aforementioned measurement means may further comprise amplification means comprising an analog circuit for amplifying the differentiated value from which the initial value has been subtracted.

In addition, The sensor of the present invention utilizing ATR may further comprise filtration means for performing a filtration process on the differentiated value.

The expression "performing a filtration process on the differentiated value," in addition to performing the filtration process on the differentiated value itself, includes performing the filtration process on the photodetection signals that are used for calculating the differentiated value, performing the filtration process on the differentiated value from which an initial value has been subtracted, and so on.

In the sensor of the present invention, the filtration means can employ, for example, a low-pass filter that allows a signal of frequency 100 Hz or less to pass through it. The low-pass filter may be a filter that allows a signal of frequency 10 Hz or less to pass through it.

According to the sensor of the present invention utilizing ATR, the photodetection means in the form of an array, consisting of a plurality of light-receiving elements juxtaposed, is employed and the photodetection signals output from the light-receiving elements are differentiated in the juxtaposed direction of the light-receiving elements by differentiation means. A change with the lapse of time in the differentiated value is measured to analyze the properties of a sample. Because of this, the initial value of a differentiated value is first measured. Every time a differentiated value is measured, the initial value is subtracted from the differentiated value output from the differentiation means. As a result, the differentiated value from which the initial value has been subtracted contains no fluctuation in an absolute value corresponding to the positional relationship between the photodetector element and a dark line, and becomes a value reflecting only a change with the lapse of time in the differentiated value from the time of the start of measurements. Therefore, the value after the subtraction is small in absolute value, compared with a differentiated value on which such subtraction is not done, and can be amplified by a sufficiently high amplification factor. Thus, a change with the lapse of time in a differentiated value can be measured with high sensitivity and an accurate analysis of a sample can be made.

BRIEF DESCRIPTION OF THE DRAWINGS

The present invention will be described in further detail with reference to the accompanying drawings wherein:

FIG. 3A is a graph showing the relationship between the incidence angle of a light beam and the intensity of the light beam, obtained according to the surface plasmon resonance sensor shown in FIG. 1;

FIG. 3B is a diagram showing a photodiode array employed in the surface plasmon resonance sensor shown in FIG. 1.

FIG. 3C is a graph showing the relationship between the incidence angle of the light beam and the differentiated value of the output of photodetection means;

FIG. 6 is a block diagram showing the electrical construction of the surface plasmon resonance sensor shown in FIG. 5;

FIG. 12 is a block diagram showing the electrical construction of the surface plasmon resonance sensor shown in FIG. 11; and FIG. 13 is a side view showing a leaky mode sensor constructed according to a fifth embodiment of the present invention.

DESCRIPTION OF THE PREFERRED EMBODIMENTS

Figure 1:
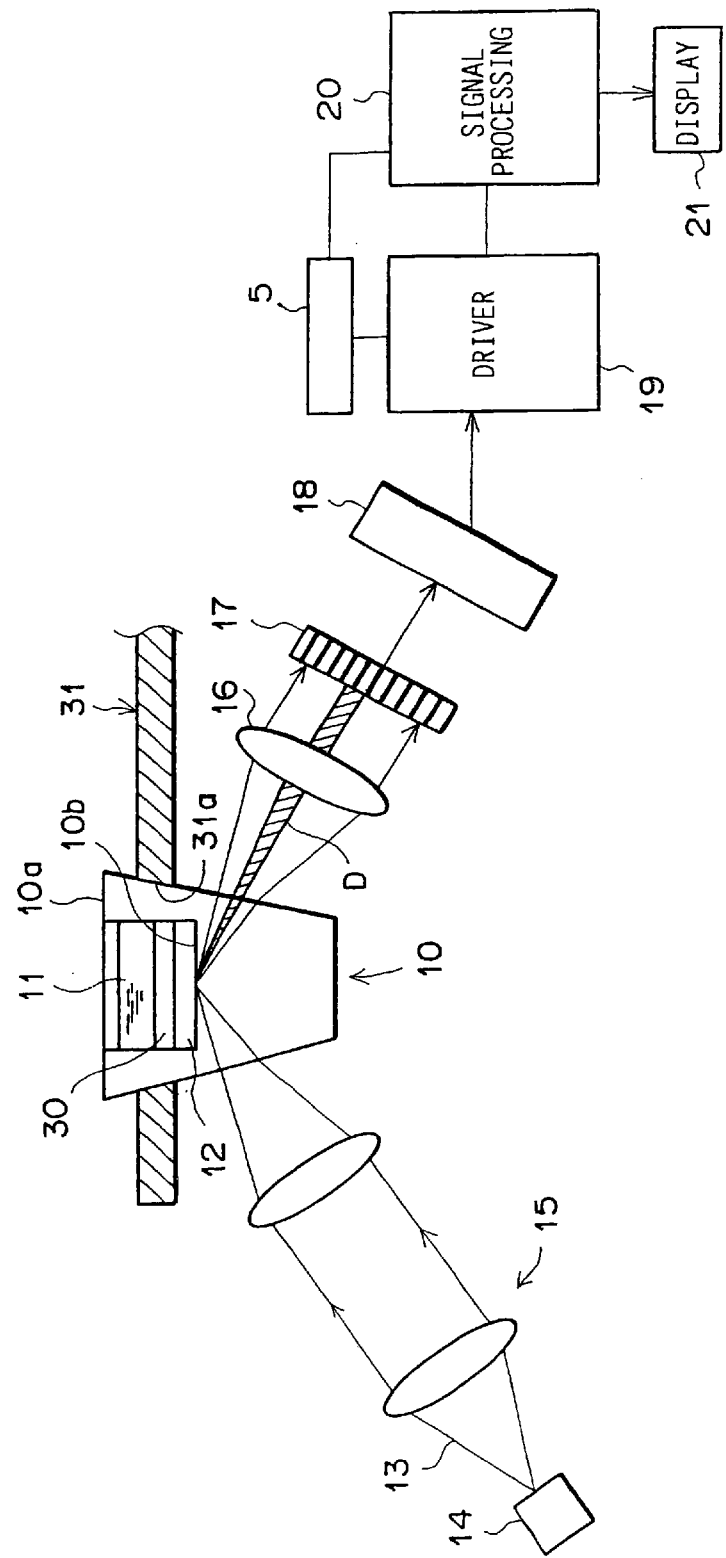
FIG. 1 is a side view showing a surface plasmon resonance sensor constructed according to a first embodiment of the present invention.

Referring now in greater detail to the drawings and initially to FIG. 1, there is shown a surface plasmon resonance sensor in accordance with a first embodiment of the present invention. The surface plasmon resonance sensor has a dielectric block 10 and a metal film 12. The dielectric block 10 is formed, for example, into the shape of a generally quadrangular pyramid, having a portion thereof cut out. The metal film 12 is formed on a surface (top surface in FIG. 1) of the dielectric block 10, and is composed, for example, of gold, silver, copper, aluminum, etc.

The dielectric block 10 is formed, for example, from transparent resin, etc., and is thickened at a portion 10a thereof to form a sample holder portion in which a liquid sample 11 is stored. In the first embodiment, a sensing medium 30 (which is to be described later) is placed on the metal film 12.

The dielectric block 10 and the metal film 12 constitute a disposable measuring chip. A plurality of measuring chips are fitted in chip holding holes 31a formed in a turntable 31, respectively. With the dielectric blocks 10 thus fitted in the chip holding holes 31a of the turntable 31, the turntable 31 is intermittently rotated by a predetermined angle at a time. If a dielectric block 10 is stopped at a predetermined position, the liquid sample 11 is dropped into the dielectric block 10 and held within the sample holding portion 10a. If the turntable 31 is further rotated by a predetermined angle, the dielectric block 10 is moved to the measuring position shown in FIG. 1 and is stopped there.

The surface plasmon resonance sensor of the first embodiment, in addition to the dielectric block 10, is equipped with a light source 14, which consists of a semiconductor laser, etc., for emitting a light beam 13; an optical system 15 for making the light beam 13 enter the dielectric block 10 so that various angles of incidence are obtained with respect to an interface 10b between the dielectric block 10 and the metal film 12; and a collimator lens 16 for collimating the light beam 13 satisfying total internal reflection at the interface 10b. The surface plasmon resonance sensor is further equipped with photodetection means 17 for detecting the collimated light beam 13; a differential amplifier array (differentiation means) 18 connected to the photodetection means 17; a driver (measurement means) 19; a signal processing section 20 constructed of a computer system, etc.; display means 21 connected to the signal processing section 20; and a correction circuit 5 connected to the signal processing section 20 and the driver 19.

Figure 2:
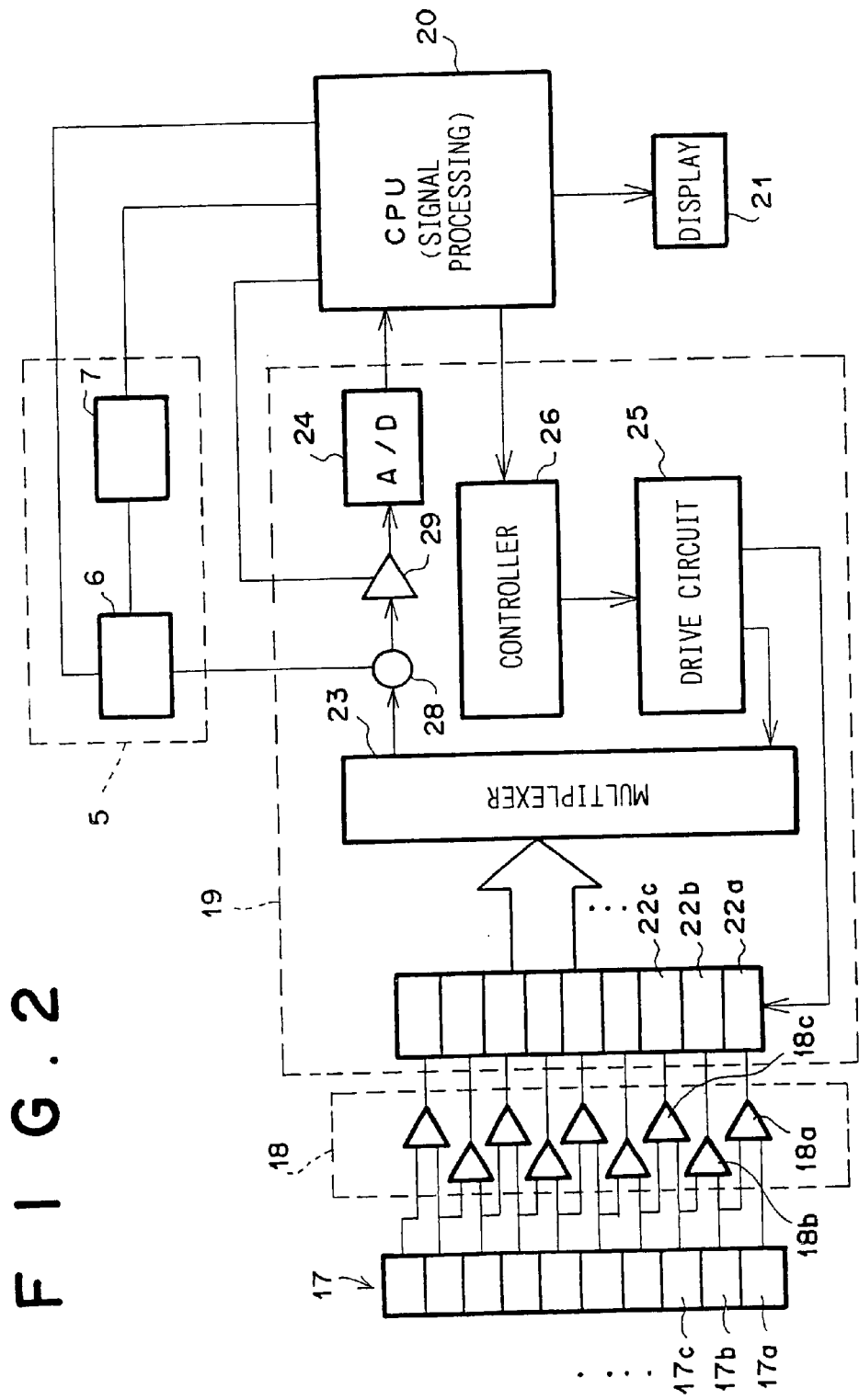
FIG. 2 is a block diagram showing the electrical construction of the surface plasmon resonance sensor shown in FIG. 1.

FIG. 2 shows the electrical construction of the surface plasmon resonance sensor shown in FIG. 1. As shown in FIG. 2, the driver 19 is constructed of sample holding circuits 22a, 22b, 22c, . . . for holding outputs of the differential amplifiers 18a, 18b, 18c, . . . of the differential amplifier array 18; a multiplexer 23 to which outputs of the sample holding circuits 22a, 22b, 22c, . . . are input; and an A/D converter 24 for digitizing the output of the multiplexer 23 and then inputting the digitized output to the signal processing section 20. The driver 19 is further constructed of a drive circuit 25 for driving the multiplexer 23 and the sample holding circuits 22a, 22b, 22c, . . . ; a controller 26 for controls operation of the drive circuit 25 in response to a control signal from the signal processing section 20; a subtracter 28 for subtracting the initial value of a differentiated value output from the correction circuit 5, from a differentiated value I' output from the multiplexer 23; and an amplifier 29 for amplifying output of the subtracter 28. The amplifier 29 is controlled by the signal processing section 20 and can select any one of amplification factors of 1, 10, and 100.

The correction circuit 5 consists of a D/A converter 7 for converting output of the signal processing section 20 to an analog signal, and an attenuator 6 for attenuating output of the D/A converter 7. The attenuator 6 is controlled by the signal processing section 20 and can select anyone of attenuation factors of 1, 1/10, and 1/100.

As shown in FIG. 1, the light beam 13 emitted divergently from the laser light source 14 is converged on the interface 10b between the dielectric block 10 and the metal film 12 by the optical system 15. Thus, the light beam 13 contains components incident at various incidence angles θ with respect to the interface 10b. Note that the incidence angles θ are equal to or greater than a critical angle of incidence at which total internal reflection takes place. Hence, the light beam 13 is reflected at the interface 10b so that it satisfies total internal reflection. The reflected light beam 13 contains components reflected at various angles.

Note that the light beam 13 is p-polarized and then strikes the interface 10b. For this reason, the laser light source 14 needs to be disposed so that the polarization direction thereof becomes a predetermined direction. Alternatively, the direction of polarization of the light beam 13 may be controlled with a wavelength plate, a polarizing plate, etc.

The light beam satisfying total internal reflection at the interface 10b is collimated by the collimator lens 16 and is detected by the photodetection means 17. The photodetection means 17 in the first embodiment is a photodiode array consisting of a plurality of photodiodes 17a, 17b, 17c, . . . juxtaposed in a row. As shown in FIG. 1, the direction in which the photodiodes are juxtaposed is approximately perpendicular to the traveling direction of the collimated light beam 13. Therefore, each of the components of the light beam 13 satisfying total internal reflection at various angles at the interface 10b are received by the different photodiodes 17a, 17b, 17c, . . . , respectively.

The outputs of the photodiodes 17a, 17b, 17c, . . . are input to the differential amplifiers 18a, 18b, 18c, . . . of the differential amplifier array 18. Note that the outputs of two adjacent photodiodes are input in common to a single differential amplifier. Therefore, the outputs of the differential amplifiers 18a, 18b, 18c, . . . are considered to be values obtained by differentiating the photodetection signals output from the photodiodes 17a, 17b, 17c, . . . , in the direction where the photodiodes are juxtaposed.

The outputs of the differential amplifiers 18a, 18b, 18c, . . . are held at predetermined timings by the sample holding circuits 22a, 22b, 22c, . . . , respectively, and are input to the multiplexer 23. The multiplexer 23 outputs the held outputs of the differential amplifiers 18a, 18b, 18c, . . . in a predetermined order. At this time, the subtracter 28 is not operated and the amplifier 29 has been set at an amplification factor of 10. In this state, the outputs of the differential amplifiers 18a, 18b, 18c, . . . are amplified by the amplifier 29 and are input to the A/D converter 24. The A/D converter 24 digitizes these outputs and then inputs the digitized signals to the signal processing section 20. Note that the circuits from the operational amplifier array 18 to the stage previous to the A/D converter 24, that is, the operational amplifier array 18, the sample holding circuits 22a, 22b, 22c, . . . , the subtracter 28, and the amplifier 29 are constructed by analog circuits.

FIG. 3A shows the relationship between the incidence angle θ of the light beam 13 with respect to the interface 10b and the above-mentioned light intensity I. Light, incident at a specific angle $\theta_{sp}$ on the interface 10b between the metal film 12 and the sample 11, excites surface plasmon at the interface 10b. Because of this, for the light incident at the specific angle $\theta_{sp}$, the intensity I of the reflected light drops sharply. That is, the specific incidence angle $\theta_{sp}$ is an angle of incidence at which ATR occurs. At the specific incidence angle $\theta_{sp}$, the reflected-light intensity I becomes the minimum value. The sharp drop in the reflected-light intensity I is observed as a dark line in the reflected light, as shown at D in FIG. 1.

FIG. 3B shows the direction in which the photodiodes 17a, 17b, 17c, . . . are juxtaposed. As described previously, the positions of the photodiodes 17a, 17b, 17c, . . . juxtaposed perpendicular to the reflected light correspond to the above-mentioned incidence angles θ.

FIG. 3C shows the relationship between the juxtaposed positions of the photodiodes 17a, 17b, 17c, . . . (i.e., the incidence angles θ) and the outputs I' of the differential amplifiers 18a, 18b, 18c, . . . (i.e., differentiated values of reflected-light intensities I).

Prior to measurement, the signal processing section 20 performs a process of setting an initial value I'r for a differentiated value I'. The signal processing section 20 first sets the amplification factor of the amplifier 29 at 10 and the attenuation factor of the attenuator 6 at 1/10. Based on the differentiated value I' (×10) input from the A/D converter 24, the signal processing section 20 selects a differential amplifier of the differential amplifiers 18a, 18b, 18c, . . . which is outputting a differentiated value I'min near a point where a change in the reflected-light intensity I makes a transition from decrease to increase, that is, a differentiated value I'min closest to the differentiated value I'=0 corresponding to the specific incidence angle $\theta_{sp}$ at which ATR occurs. In the example shown in FIG. 3, the differential amplifier 18e is selected.

The differentiated value I'min output from the differential amplifier 18e is amplified at the amplifier 29 by a factor of 10 and is input to the signal processing section 20. The signal processing section 20 outputs an initial value I'r of the same voltage as the differentiated value I'min (×10) to the D/A converter 7. The analog output (I'r) of the D/A converter 7 is attenuated by a factor of 1/10 with the attenuator 6 which is an analog circuit. In the subtracter 28 which is an analog circuit, the output of the attenuator 6 is subtracted from the differentiated value I'min output from the multiplexer 23. Because of this, a value of the subtraction of the initial value I'r (×1/10) from the differentiated value I'min output from the differential amplifier 18e is input again to the signal processing section 20. The signal processing section 20 makes fine adjustments to the voltage of the initial value I'r so that the value of an input signal becomes 0, and then stores the initial value I'r in a memory section (not shown). The fine adjustments to the initial value I'r can remove the influence of offsets, etc., of the amplifier 29, the A/D converter 24, the signal processing section 20, the D/A converter 7, the attenuator 6, and the subtracter 28.

Note that by setting the amplification factor of the amplifier 20 at 10 and the attenuation factor of the attenuator 6 at 1/10, fine adjustments to the initial value can be made even if a converter with a smaller number of bits is used as the D/A converter 7. In addition, in the case where the absolute value of the differentiated value I' output from the multiplexer 23 is great, the amplification factor of the amplifier 29 can be set at 1, and at the same time, the attenuation factor of the attenuator 6 can also be set at 1.

Figure 4:
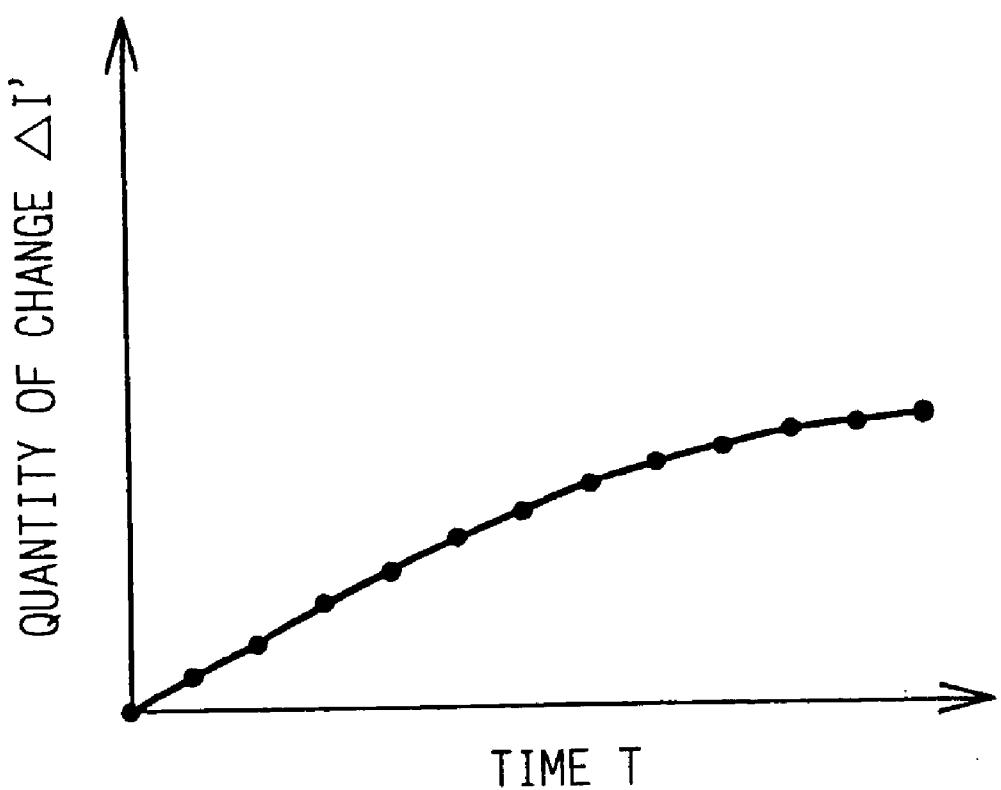
FIG. 4 is a graph showing the relationship between time and a quantity of change in the differentiated value.

After the setting of the initial value I'r, the signal processing section 20 sets the amplification factor of the amplifier 29 at 100 and starts measurements. Note the attenuation factor of the attenuator 6 is maintained at 1/10. The signal processing section 20 causes the multiplexer 23 to output the differentiated value I' output from the differential amplifier 18e, through the controller 26 and the drive circuit 25. The signal processing section 20 also outputs the initial value I'r being stored in the memory section (not shown) to the D/A converter 7. The initial value I'r is attenuated by a factor of 1/10 at the attenuator 6, and at the subtracter 28, the attenuated initial value I'r is subtracted from the differentiated value I'. In this manner, a quantity of change ΔI' in the differentiated value I' is output from the subtracter 28. The quantity of change ΔI' is multiplied at the amplifier 29 by 100 and is input to the A/D converter 24, in which it is digitized. The signal processing unit 20 measures the quantity of change ΔI' multiplied by 100. Each quantity of change ΔI' multiplied by 100 is displayed as shown in FIG. 4 by the display means 21.

At the time of the first measurement, the value that is displayed is approximately 0 regardless of the magnitude of the differentiated value I' output from the differential amplifier 18e. Thereafter, each time a predetermined time elapses, a quantity of change ΔI' in the differentiated value I' from the first measurement to the next measurement is amplified by a factor of 100 and is displayed on a graph by the display means 21.

If the dielectric constant or refractive index of the substance in contact with the metal film 12 (see FIG. 1) changes and therefore the curve in FIG. 3A is shifted in a horizontal direction, the differentiated value I' is increased or decreased according to the shift. Therefore, by continuously measuring a quantity of change ΔI' in the differentiated value I' with the lapse of time, a change in the refractive index of the substance in contact with the metal film 12, that is, a change in the property of the substance, can be detected.

Particularly, in the first embodiment, the sensing medium 30 that couples with a specific substance in the liquid sample 11 is placed on the metal film 12, and according to the coupled state, the refractive index of the sensing medium 30 changes. Therefore, by continuously measuring a quantity of change ΔI' in the differentiated value I', how the coupled state changes can be detected.

As described above, the first embodiment employs the photodiode array, consisting of a plurality of photodiodes 17a, 17b, 17c, . . . juxtaposed in a row, as the photodetection means 17. Therefore, even if the curve in FIG. 3A is greatly shifted in a horizontal direction according to a change in the liquid sample 11, the dark line can be detected. That is, the use of the photodetection means 17 in the form of an array makes it possible to secure a large dynamic range of measurements.

Note that the differential amplifier array 18, consisting of differential amplifiers 18a, 18b, 18c, . . . , may be replaced with a single differential amplifier. In this case, the outputs of the photodiodes 17a, 17b, 17c, . . . are switched by a multiplexer so that two adjacent outputs are input in sequence to the single differential amplifier.

In the sensor according to the first embodiment, as described above, at the time of the start of measurements the signal processing section 20 selects the differential amplifier 18e that has a differentiated value I'min near a point where a change in the reflected-light intensity I makes a transition from decrease to increase, that is, a differentiated value I'min closest to the differentiated value I'=0 corresponding to the specific incidence angle $\theta_{sp}$ at which ATR takes place. Based on the differentiated value output from the differential amplifier 18e, an initial value of the differentiated value is calculated and stored in the memory section (not shown). Thereafter, each time a predetermined time elapses, a quantity of change ΔI' in the differentiated value I' is first calculated by subtracting the initial value from the differentiated value I' output from the differential amplifier 18e. Then, the a quantity of change ΔI' is amplified by a factor of 100 and is digitized by the A/D converter 24. The digitized quantity of change ΔI' is displayed on the display means 21. In this manner, a change with the lapse of time in the differentiated value can be measured with high sensitivity without saturating subsequent electric circuits. Note that while, in the first embodiment described above, the dielectric block 10 and the metal film 12 constitute a disposable measuring chip, the same advantages as the first embodiment can be obtained, even in the case where the dielectric block 10 is incorporated in the main body of the surface plasmon resonance sensor.

Figure 5:
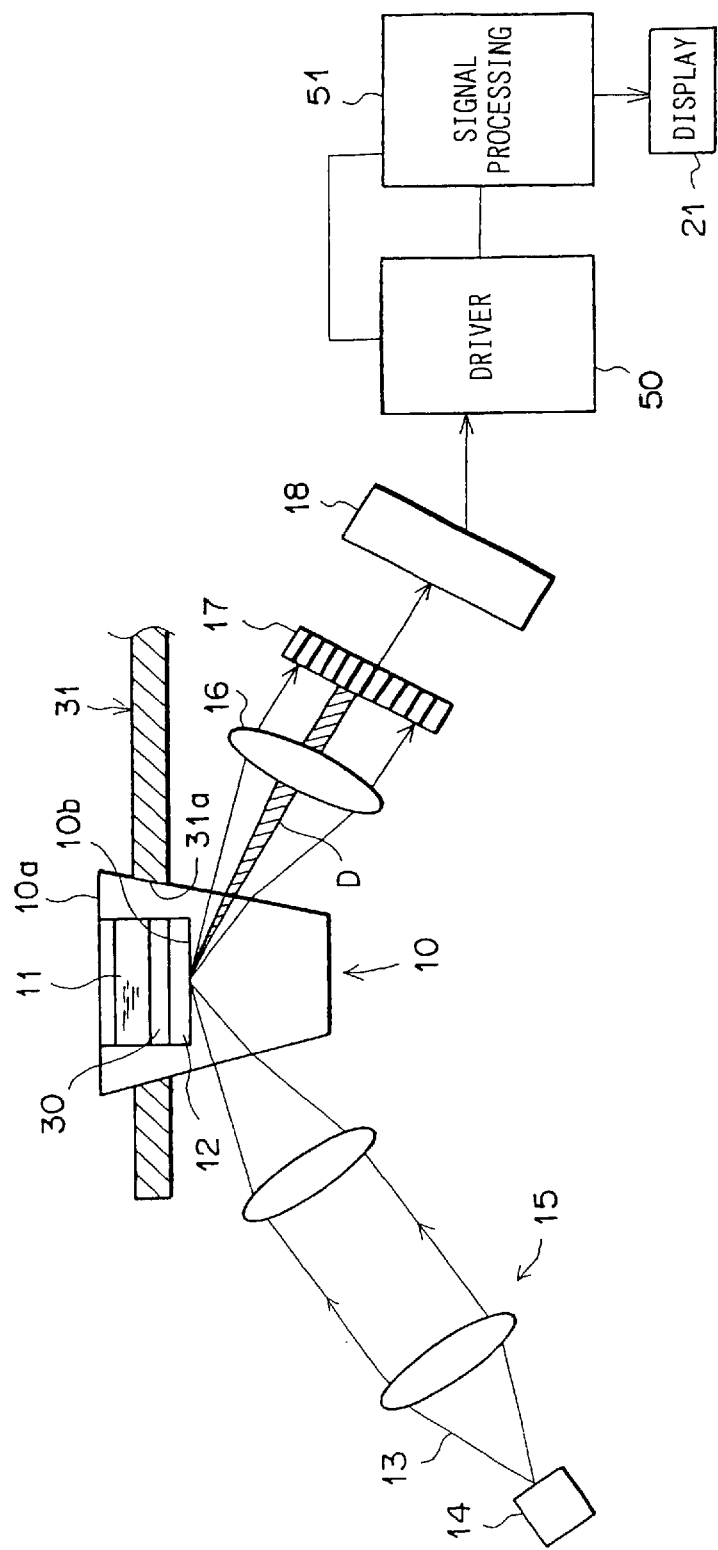
FIG. 5 is a side view showing a surface plasmon resonance sensor constructed according to a second embodiment of the present invention.
Figure 7:
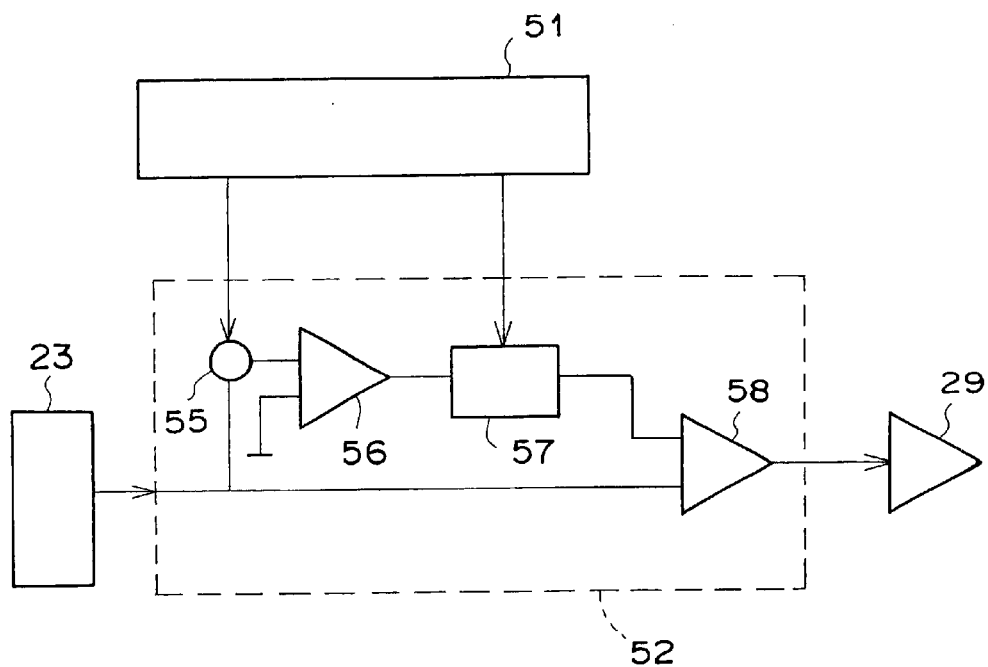
FIG. 7 is a block diagram showing the zero point correction circuit of the surface plasmon resonance sensor shown in FIG. 5.

FIGS. 5 to 7 show a surface plasmon resonance sensor constructed according to a second embodiment of the present invention. Note in FIGS. 5 and 6 that the same reference numerals are applied to the same parts as those in FIGS. 1 and 2, and that a description thereof will not be given unless particularly necessary.

As illustrated in FIG. 5, the surface plasmon resonance sensor of the second embodiment is equipped with a dielectric body 10, a laser light source 14, an optical system 15, and a collimator lens 16 for collimating a light beam 13. The surface plasmon resonance sensor is further equipped with photodetection means 17 for detecting the collimated light beam 13; a differential amplifier array or differentiation means 18 connected to the photodetection means 17; a signal processing section 51 constructed of a computer system and a driver (measurement means) 50; and display means 21 connected to the signal processing section 51.

FIG. 6 shows the electrical construction of the surface plasmon resonance sensor of the second embodiment shown in FIG. 5. As shown in FIG. 6, the driver 50 is constructed of sample holding circuits 22a, 22b, 22c, . . . ; a multiplexer 23 to which the outputs of the sample holding circuits 22a, 22b, 22c, . . . are input; and an A/D converter 24 for digitizing the output of the multiplexer 23 and then inputting the digitized output to the signal processing section 51. The driver 50 is further constructed of a drive circuit 25 for driving the multiplexer 23 and the sample holding circuits 22a, 22b, 22c, . . . ; a controller 26 for controls operation of the drive circuit 25 in response to a control signal from the signal processing section 51; a zero point correction circuit 52 for outputting a difference between a differentiated value I' output from the multiplexer 23 and an initial value of the differentiated value set at the time of the first measurement; and an amplifier 29 for amplifying output of the zero point correction circuit 52.

As shown in FIG. 7, the zero point correction circuit 52 is constructed of a switch 55 connected to the signal processing circuit 51; a first differentiator 56 for outputting a difference between the initial value of a differentiated value and a zero point; a sample holding circuit 57 for holding a value output from the differentiator 56; and a second differentiator 58 for calculating a difference between a differentiated value measured and the initial value of the differentiated value. These circuits of the zero point correction circuit 52 are analog circuits. The other terminal of the differentiator 56 not connected with the switch 55 is connected to ground.

Prior to measurements, the signal processing section 51 performs a process of setting an initial value I'r for the differentiated value I'. The signal processing section 51 first sets the amplification factor of the amplifier 29 at 10. Based on the differentiated value I' (×10) input from the A/D converter 24, the signal processing section 51 selects a differential amplifier of the differential amplifiers 18a, 18b, 18c, . . . which is outputting a differentiated value I'min near a point where a change in the reflected-light intensity I makes a transition from decrease to increase, that is, a differentiated value I'min closest to the differentiated value I'=0 corresponding to the specific incidence angle $\theta_{sp}$ at which ATR occurs. The differential amplifier 18e, for example, is selected.

Next, the signal processing section 51 causes the switch 55 of the zero point correction circuit 52 to be on. The first differentiator 56 outputs the difference between the differentiated value I'min, output from the differential amplifier 18e, and a zero point, that is, an initial value I'r. The initial value I'r (difference) is held by the sample holding circuit 57. Thereafter, the signal processing section 51 causes the switch 55 to be off.

After the setting of the initial value I'r, the signal processing section 51 sets the amplification factor of the amplifier 29 at 100 and starts measurements. The signal processing section 51 causes the multiplexer 23 to output the differentiated value I' output from the differential amplifier 18e, through the controller 26 and the drive circuit 25. Because the switch 55 is off, the differentiated value I' is output only to the differential circuit 58. The second differentiator 58 outputs the difference between the differentiated value I' and the initial value I'r. That is, a quantity of change ΔI' in the differentiated value I' is output. The quantity of change ΔI' is multiplied at the amplifier 29 by 100 and is input to the A/D converter 24, in which it is digitized. The signal processing unit 51 measures the quantity of change ΔI' multiplied by 100. The measured value is displayed by the display means At the time of the first measurement, the value that is displayed is approximately 0 regardless of the magnitude of the differentiated value I' output from the differential amplifier 18e. Thereafter, every time a predetermined time elapses, a quantity of change ΔI' in the differentiated value I' from the first measurement to the next measurement is amplified by a factor of 100 and is displayed on the display means 21.

In the sensor according to the second embodiment, as described above, at the time of the start of measurements the signal processing section 51 selects the differential amplifier 18e that is outputting a differentiated value I'min near a point where a change in the reflected-light intensity I makes a transition from decrease to increase, that is, a differentiated value I'min closest to the differentiated value I'=0 corresponding to the specific incidence angle $\theta_{sp}$ at which ATR takes place. The difference (initial value) between the differentiated value output from the differential amplifier 18e and a zero point, is held by the sample holding circuit 57. Every time a predetermined time elapses, a quantity of change ΔI' in the differentiated value I' is found by finding the difference between the differentiated value I' output from the differential amplifier 18e and the initial value. Then, the quantity of change ΔI' is amplified by a factor of 100 and is digitized by the A/D converter 24. The digitized quantity of change ΔI' is displayed on the display means 21. In this way, a change with the lapse of time in the differentiated value can be measured with high sensitivity without saturating subsequent electric circuits. As a result, an accurate analysis of a sample can be made.

Figure 8:
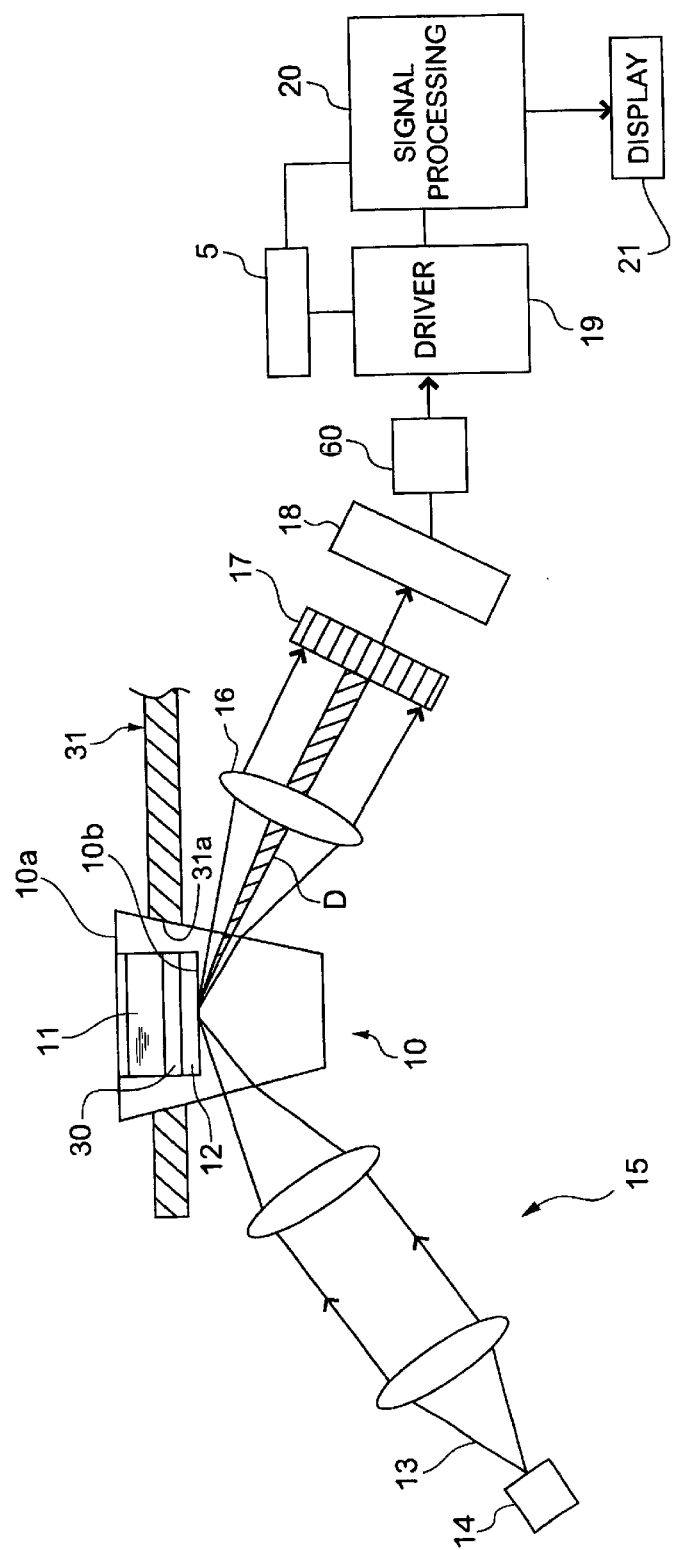
FIG. 8 is a side view showing a surface plasmon resonance sensor constructed according to a third embodiment of the present invention.
Figure 9:
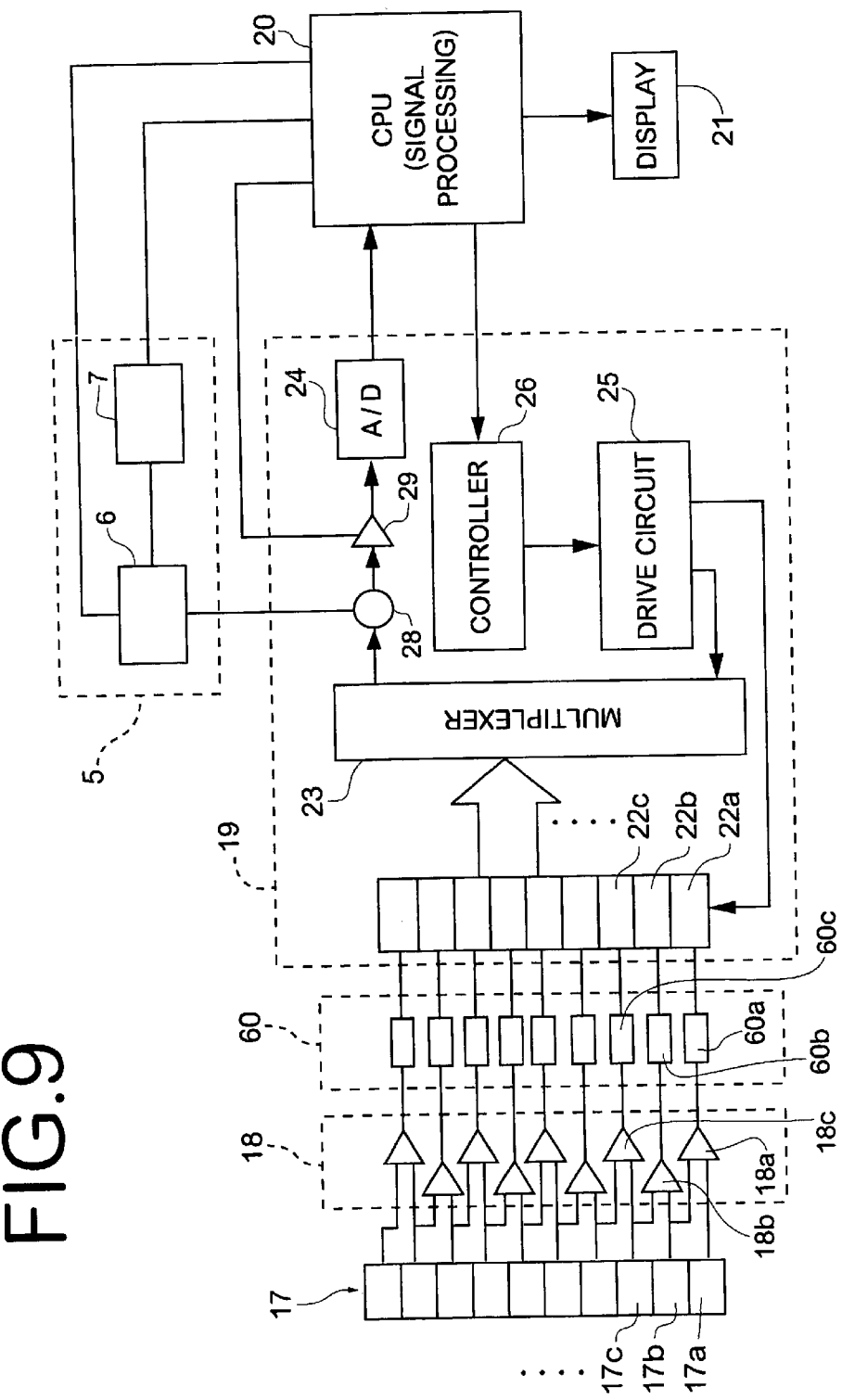
FIG. 9 is a block diagram showing the electrical construction of the surface plasmon resonance sensor shown in FIG. 8.

FIGS. 8 to 10 show a surface plasmon resonance sensor constructed according to a third embodiment of the present invention. In the surface plasmon resonance sensor of the third embodiment, a filter section 60 is added to the surface plasmon resonance sensor of the first embodiment shown in FIG. 1. The remaining construction is the same as the surface plasmon resonance sensor of the first embodiment. Note in FIGS. 8 and 9 that the same reference numerals are applied to the same parts as those in FIGS. 1 and 2, and that a description thereof will not be given unless particularly necessary.

Figure 10A:
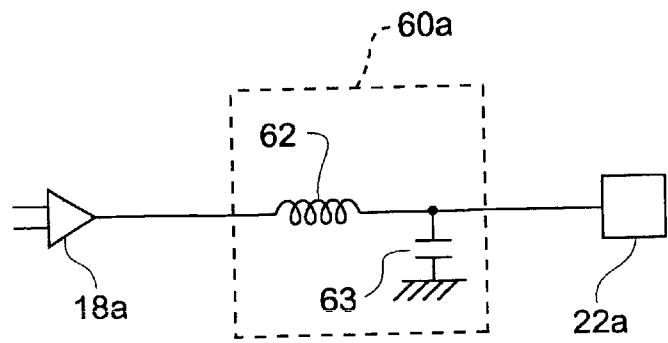
FIGS. 10A and 10B are circuit diagrams showing a low-pass filter employed in the surface plasmon resonance sensor shown in FIG. 8.

As shown in FIGS. 8 and 9, the filter section 60 is constructed of low-pass filters 60a, 60b, 60c, . . . , and is provided between a differential amplifier array 18 and a driver 19. The low-pass filters 60a, 60b, 60c, . . . are disposed between differential amplifiers 18a, 18b, 18c, . . . and sample holding circuits 22a, 22b, 22c, . . . , respectively. Each low-pass filter is an analog type band-pass filter consisting of a coil 62 and a capacitor 63, as shown in FIG. 10A. The low-pass filter allows only a signal of frequency 100 Hz or less to pass through it.

In the surface plasmon resonance sensor of the third embodiment, only signals of 100 Hz or less, contained in the differentiated values I' output from the differential amplifiers 18a, 18b, 18c, . . . , are passed through the low-pass filters 60a, 60b, 60c, . . . and are output to the sample holding circuits 22a, 22b, 22c, . . . After the sample holding circuits 22a, 22b, 22c, . . . , the same process as that in the first embodiment is performed on the differentiated values I' from which signals exceeding 100 Hz have been removed by the low-pass filters 60a, 60b, 60c, . . . A quantity of change ΔI' in the differentiated value I' is measured, and is displayed on the display means 21.

In this manner, in the third embodiment, noise with a frequency greater than 100 Hz, superposed at photodiodes 17a, 17b, 17c, . . . and differential amplifiers 18a, 18b, 18c, . . . , is removed. Note that the differentiated value I' is not contained in a high-frequency signal, so that only noise is removed. A signal-to-noise (S/N) ratio for the differentiated value I' is enhanced, and consequently, a S/N ratio for a quantity of change ΔI' in the differentiated value I' is also enhanced. Thus, a change with the lapse of time in the differentiated value can be measured with higher sensitivity.

If the passing bands of the low-pass filters 60a, 60b, 60c, . . . are 10 Hz or less, noise with a frequency grater than 10 Hz can be removed and therefore a S/N ratio for the differentiated value I' can be further enhanced.

Figure 10B:
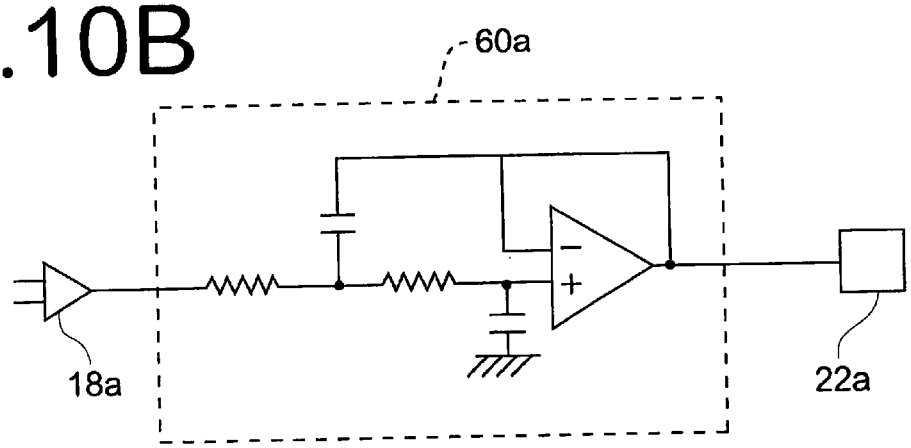

Note that the low-pass filters 60a, 60b, 60c, . . . may use filters that employ an operational amplifier, as shown in FIG. 10B. In addition, a variable band-pass filter capable of varying its wavelength passing band may be employed according to the frequency band of noise having a possibility of being contained in the differentiated value I'. Furthermore, the low-pass filters 60a, 60b, 60c, . . . may be disposed at a position other than between the differential amplifiers 18a, 18b, 18c, . . . and the sample holding circuits 22a, 22b, 22c, . . . For instance, they may be provided between the sample holding circuits 22a, 22b, 22c, . . . and the multiplexer 23, or between the photodiodes 17a, 17b, 17c, . . . and the differential amplifiers 18a, 18b, 18c, . . . In the case where the low-pass filters are provided after the multiplexer 23, a single low-pass filter may be provided. In this case, the filter section 60 can be structurally simplified.

Figure 11:
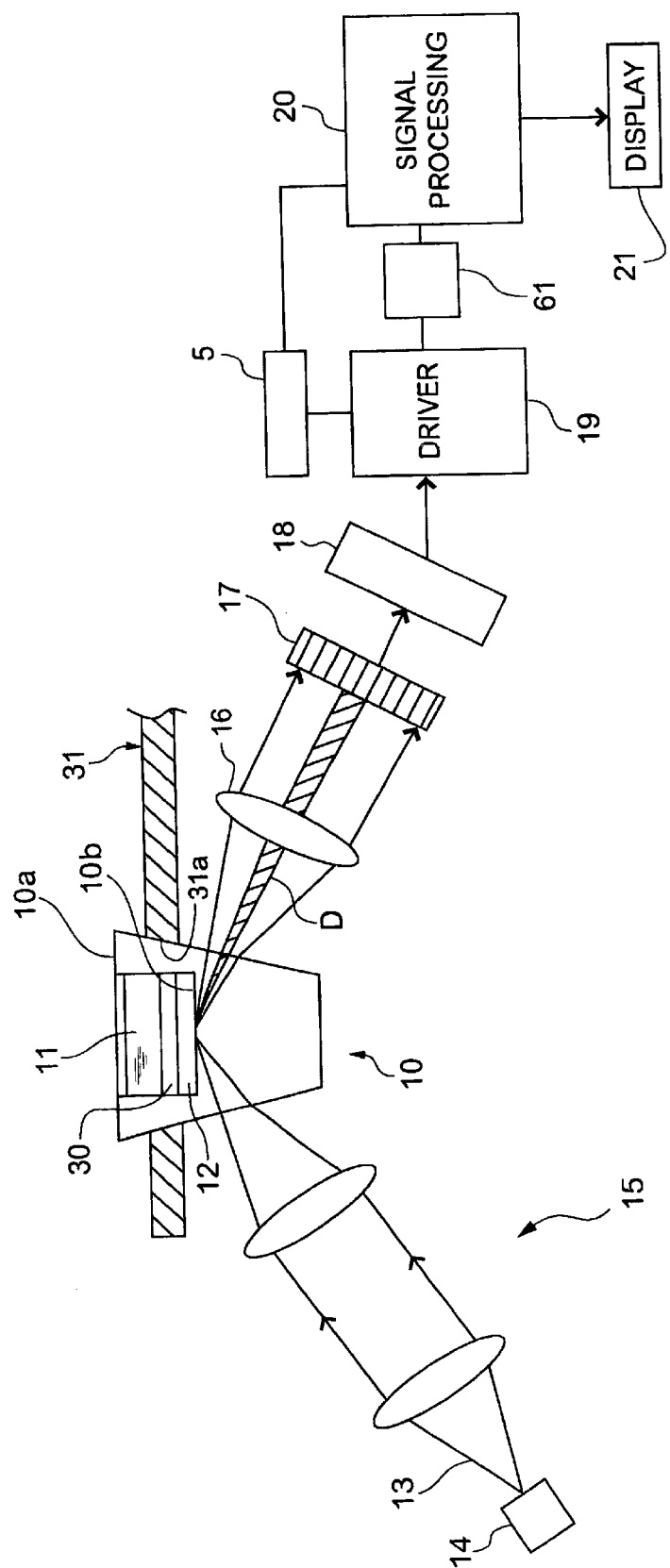
FIG. 11 is a side view showing a surface plasmon resonance sensor constructed according to a fourth embodiment of the present invention.

FIGS. 11 and 12 show a surface plasmon resonance sensor constructed according to a fourth embodiment of the present invention. In the surface plasmon resonance sensor of the fourth embodiment, a filter section 61 is added to the surface plasmon resonance sensor of the first embodiment shown in FIG. 1. The remaining construction is the same as the surface plasmon resonance sensor of the first embodiment. Note in FIGS. 11 and 12 that the same reference numerals are applied to the same parts as those in FIGS. 1 and 2, and that a description thereof will not be given unless particularly necessary.

The filter section 61 is a digital type low-pass filter that permits only a signal of frequency 100 Hz or less to pass through it. As shown in FIGS. 11 and 12, the filter section 61 is provided between a driver 19 and a signal processing section 20. The digital type filter constituting the filter section 61 can employ a Butterworth filter, in which the damping characteristic in the passing band is the flattest in direct current and the damping characteristics in the passing band and the preventing band both change monotonously, or a Bessel filter, in which the group delay characteristic in the passing band is the flattest in direct current and the damping characteristics in the passing band and the preventing band both change monotonously. The digital type filter can also use an addition averaging circuit, which calculates an addition average value of the signal values of n signals before and behind a predetermined signal and outputs the addition average value, or a weighting circuit, which calculates a signal value by performing a weighting process on n signals before and behind a predetermined signals and outputs the signal value.

In the surface plasmon resonance sensor of the fourth embodiment, only signals of 100 Hz or less, contained a quantity of change ΔI' in the differentiated values I' output from the A/D converter 24 of the driver 19, are passed through the filter section 61 and are output to the signal processing section 20. In the signal processing 20, the same process as that in the first embodiment is performed and a quantity of change ΔI' in the differentiated values I' is displayed on the display means 21.

In this manner, in the fourth embodiment, noise with a frequency greater than 100 Hz, superposed before it is input to the signal processing section 20, is removed from a quantity of change ΔI' in the differentiated values I'. Note that a quantity of change ΔI' in the differentiated value I' is not contained in a high-frequency signal, so that only noise is removed. A signal-to-noise (S/N) ratio for a quantity of change ΔI' in the differentiated value I' is enhanced. Thus, a change with the lapse of time in the differentiated value can be measured with higher sensitivity.

In addition, if the passing band of the filter section 61 is 10 Hz or less, noise with a frequency grater than 10 Hz can be removed and therefore a S/N ratio for a quantity of change ΔI' in the differentiated value I' can be further enhanced.

Note that in each of the embodiments described above, the dielectric blocks 10 and the metallic film 12 constitute the disposable measurement chip. However, even in a case in which the dielectric blocks 10 are not formed as chips, but rather built in to the surface plasmon resonance sensor, similar effects can be obtained.

FIG. 13 shows a sensor constructed according to a fifth embodiment of the present invention. Note in the figure that the same reference numerals are applied to the same parts as those in FIG. 1, and that a description thereof will not be given unless particularly necessary.

The sensor of the fifth embodiment utilizing ATR is a leaky mode sensor. As with the first embodiment, the fifth embodiment is constructed so that it employs a plurality of dielectric blocks 10 as measuring chips. Each dielectric block 10 has a cladding layer 40 on a surface thereof (e.g., the top surface in FIG. 11), and an optical waveguide layer 41 is formed on the cladding layer 40.

The dielectric block 10 is formed, for example, from synthetic resin, or optical glass such as BK7, etc. The cladding layer 40 is formed into the shape of a thin film from a dielectric lower in refractive index than the dielectric block 10, or a metal such as gold, etc. The optical waveguide layer 41 is also formed into the shape of a thin film from a dielectric higher in refractive index than the cladding layer 40, such as polymethylmethacrylate (PMMA). The cladding layer 40 is 36.5 nm in thickness when it is formed from a thin gold film. The optical waveguide layer 41 is about 700 nm in thickness when it is formed from PMMA.

In the leaky mode sensor of the fifth embodiment, if a light beam 13 emitted from a laser light source 14 strikes the cladding layer 40 through the dielectric block 10 at angles of incidence equal to or greater than an angle of incidence at which total internal reflection takes place, the light beam 13 satisfies total internal reflection at an interface 10b between the dielectric block 10 and the cladding layer 40. However, light with a specific wave number, incident on the optical waveguide layer 41 through the cladding layer 40 at a specific angle of incidence, propagates in the optical waveguide layer 41 in a waveguide mode. If the waveguide mode is thus excited, the greater part of the incident light is confined within the optical waveguide layer 41, and consequently, ATR occurs in which the intensity of light satisfying total internal reflection at the interface 10b drops sharply.

Since the wave number of light propagating in the optical waveguide layer 41 depends on the refractive index of a sensing medium 30 on the optical waveguide layer 41, the refractive index of the sensing medium 30 can be measured based on the differentiated value I' output from each differential amplifier of the differential amplifier array 18.

In the fifth embodiment, as with the first embodiment, the signal processing section 20 and the correction circuit 5 perform the same process as the first embodiment on the differentiated value I' to find a quantity of change ΔI' in the differentiated value I'. Then, the quantity of change ΔI' is amplified by a factor of 100. After A/D conversion, the measured value is displayed on display means 21. In this manner, the fifth embodiment, as with the first embodiment, is capable of measuring a change with the lapse of time in the differentiated value, that is, a change with the lapse of time in the state of ATR without saturating subsequent electric circuits, and then measuring the coupled state between a target substance and the sensing medium 30.

In the subtracter 28 of the driver 19 in the first embodiment and the third through the fifth embodiments, an initial value I'r of the differentiated value I', which is an analog signal, is subtracted from the differentiated value I' which is an analog signal. If such a subtraction process is performed with digital signals, there is a fear that bit error will become great, when an amount of signal is slight. However, by employing analog signals, a result of subtraction with reduced error can be obtained even if an amount of signal is slight. In addition, because the differential amplifier array 18 and the amplifier 29 also employ analog circuits, the quantity of change ΔI', which is amplified by a factor of 100 and input to the signal processing section 20, becomes a quantity of change whose error is further reduced.

In the aforementioned embodiments, the differential amplifier 18e has been selected that has a differentiated value I'min near a point where a change in the reflected-light intensity I makes a transition from decrease to increase, that is, a differentiated value I'min closet to a differentiated value I'=0 corresponding to an incidence angle $\theta_{sp}$ at which ATR takes place. However, the present invention is not limited to differential amplifier 18e. The differential amplifier 18d or 18f, for example, may be selected and, at the time of measurements, the initial value may be subtracted. That is, even if any differential amplifier may be selected, a change with the lapse of time can be detected, if it outputs a differentiated value reflecting a change in the property of a sample. In addition, the present invention is not limited to the output of a differential amplifier. For instance, the reflected-light intensity I may be detected with a photodetector connected to a differential amplifier that outputs a differentiated value reflecting a change in the property of a sample. In this case, an initial value of the reflected-light intensity I is subtracted from the detected intensity I, and a change with the lapse of time in the intensity I is directly measured. As a modification of the fifth embodiment, it may use the zero point correction circuit 52, as with the second embodiment, or it may be provided with the filter section 60 or 61 of the third and fourth embodiments.

Finally, while the present invention has been described with reference to the preferred embodiments thereof, the invention is not to be limited to the details given herein, but may be modified within the scope of the invention hereinafter claimed.

What is claimed is:

1. A sensor utilizing attenuated total reflection, comprising:
    a dielectric block;
    a thin film layer, formed on a surface of said dielectric block, for placing a sample thereon;
    a light source for emitting a light beam;
    an optical system for making said light beam enter said dielectric block at various angles of incidence so that a condition for total internal reflection is satisfied at an interface between said dielectric block and said thin film layer;

photodetection means, comprising a plurality of light-receiving elements juxtaposed in a predetermined direction and disposed to respectively receive components of said light satisfying said total internal reflection condition at said interface, for detecting said attenuated total reflection;

differentiation means for differentiating a photodetection signal output from each of said light-receiving elements of said photodetection means, in the juxtaposed direction of said light-receiving elements, and then outputting a differentiated value; and measurement means for subtracting an initial value from the differentiated value near a point where a change in said photodetection signal in said juxtaposed direction of said light-receiving elements makes a transition from decrease to increase, and then measuring a change with the lapse of time in the differentiated value from which said initial value has been subtracted.

2. A sensor utilizing attenuated total reflection, comprising:

a dielectric block;

a thin film layer, formed on a surface of said dielectric block, for placing a sample thereon;

a light source for emitting a light beam;

an optical system for making said light beam enter said dielectric block at various angles of incidence so that a condition for total internal reflection is satisfied at an interface between said dielectric block and said thin film layer;

photodetection means, comprising a plurality of light-receiving elements juxtaposed in a predetermined direction and disposed to respectively receive components of said light satisfying said total internal reflection condition at said interface, for detecting said attenuated total reflection caused by surface plasmon resonance;

differentiation means for differentiating a photodetection signal output from each of said light-receiving elements of said photodetection means, in the juxtaposed direction of said light-receiving elements, and then outputting a differentiated value; and measurement means for subtracting an initial value from the differentiated value near a point where a change in said photodetection signal in said juxtaposed direction of said light-receiving elements makes a transition from decrease to increase, and then measuring a change with the lapse of time in the differentiated value from which said initial value has been subtracted.

3. A sensor utilizing attenuated total reflection, comprising:

a dielectric block;

a cladding layer formed on a surface of said dielectric block;

an optical waveguide layer, formed on a surface of said cladding layer, for placing a sample thereon;

a light source for emitting a light beam;

an optical system for making said light beam enter said dielectric block at various angles of incidence so that a condition for total internal reflection is satisfied at an interface between said dielectric block and said thin film layer;

photodetection means, comprising a plurality of light-receiving elements juxtaposed in a predetermined direction and disposed to respectively receive components of said light satisfying said total internal reflection condition at said interface, for detecting said attenuated total reflection caused by excitation of a waveguide mode in said optical waveguide layer;

differentiation means for differentiating a photodetection signal output from each of said light-receiving elements of said photodetection means, in the juxtaposed direction of said light-receiving elements, and then outputting a differentiated value; and measurement means for subtracting an initial value from the differentiated value near a point where a change in said photodetection signal in said juxtaposed direction of said light-receiving elements makes a transition from decrease to increase, and then measuring a change with the lapse of time in the differentiated value from which said initial value has been subtracted.

4. The sensor as set forth any of claims 1 to 3, wherein said differentiation means outputs a difference between optical signals output from two adjacent light-receiving elements of said photodetection means.

5. The sensor as set forth in any one of claims 1 to 3, wherein said photodetection means is a photodiode array.

6. The sensor as set forth in any one of claims 1 to 3, wherein said differentiation means is an analog circuit.

7. The sensor as set forth in any one of claims 1 to 3, wherein said measurement means performs said subtraction by an analog circuit, and after A/D conversion is performed on the differentiated value from which said initial value has been subtracted, said measurement is made by a digital circuit.

8. The sensor as set forth in any one of claims 1 to 3, wherein said measurement means further comprises amplification means comprising an analog circuit for amplifying the differentiated value from which said initial value has been subtracted.

9. The sensor as set forth in any one of claims 1 to 3, further comprising filtration means for performing a filtration process on said differentiated value.

10. The sensor as set forth in claim 9, wherein said filtration means is a low-pass filter that allows a signal of frequency 100 Hz or less to pass through it.

11. The sensor as set forth in claim 10, wherein said low-pass filter allows a signal of frequency 10 Hz or less to pass through it.

* * * * *